(12) United States Patent
Berbers

(10) Patent No.: US 6,607,503 B1
(45) Date of Patent: Aug. 19, 2003

(54) ARRANGEMENT FOR TRANSFERRING AN OVUM FROM A FOLLICLE

(76) Inventor: Jozefus Elbertus Johanna Maria Berbers, Jonckherenhof 7, NL-6581 GC Malden (NL)

(*) Notice: Subject to any disclaimer, the term of this patent is extended or adjusted under 35 U.S.C. 154(b) by 0 days.

(21) Appl. No.: 09/936,006

(22) PCT Filed: Mar. 10, 2000

(86) PCT No.: PCT/NL00/00164
§ 371 (c)(1),
(2), (4) Date: Jan. 4, 2002

(87) PCT Pub. No.: WO00/53108
PCT Pub. Date: Sep. 14, 2000

(30) Foreign Application Priority Data

Mar. 10, 1999 (NL) .............................. 1011522

(51) Int. Cl.[7] .................. A61M 1/00; A61M 25/00; A61M 5/32
(52) U.S. Cl. .................. 604/27; 604/264; 604/272
(58) Field of Search .................. 604/27, 35, 43–45, 604/55, 28, 272, 264, 258, 506

(56) References Cited

U.S. PATENT DOCUMENTS

| 3,762,567 | A | * | 10/1973 | Albisser | .............. | 210/532 |
|---|---|---|---|---|---|---|
| 4,202,332 | A | * | 5/1980 | Tersteegen et al. | ...... | 128/214.4 |
| 4,319,580 | A | * | 3/1982 | Colley et al. | .............. | 128/661 |
| 4,453,545 | A | * | 6/1984 | Inoue | .................. | 128/207.15 |
| 4,986,279 | A | * | 1/1991 | O'Neill | ................ | 128/754 |
| 5,160,319 | A |   | 11/1992 | Emery et al. | | |
| 5,405,321 | A | * | 4/1995 | Reeves | ................ | 604/44 |
| 6,024,693 | A | * | 2/2000 | Schock et al. | .............. | 600/18 |
| 6,196,989 | B1 | * | 3/2001 | Padget et al. | ................ | 604/27 |

FOREIGN PATENT DOCUMENTS

| DE | 3522782 A1 | 1/1987 |
|---|---|---|
| EP | 0 131 166 A1 | 1/1985 |
| WO | WO86/06968 A1 | 4/1986 |

* cited by examiner

*Primary Examiner*—Sharon Kennedy
(74) *Attorney, Agent, or Firm*—Jeffrey D. Myers

(57) ABSTRACT

An arrangement for transferring an ovum from a follicle by implementing a technique of simultaneous flushing and aspiration, the arrangement comprising a double lumen needle having an elongate needle body with a cuspidated needle end to be inserted into a follicle, the needle lumen comprising an ovum pick-up lumen for removing an ovum from a follicle, and an interior flushing lumen made of a flexible material for inserting a flushing fluid into the follicle. The flexible inner lumen is elastically deformable when the ovum is passed through the outer ovum lumen. Also disclosed is a connector body.

5 Claims, 3 Drawing Sheets

ARRANGEMENT FOR TRANSFERRING AN OVUM FROM A FOLLICLE

CROSS REFERENCE TO RELATED APPLICATIONS

This application claims benefit under 35 U.S.C. 371 to international application No. PCT/NL00/00164, filed on Mar. 10, 2000.

BACKGROUND OF THE INVENTION

The present invention relates to an arrangement for transferring an ovum from a follicle with a combined aspiration and flushing technique and in accordance with the introductory part of claim 1.

An arrangement of this type is known from Australian patent AU-B-68184/87. In this known arrangement the two tubes, that is to say, the inner tube and the outer tube, are made of stainless steel. The inner tube has an outside diameter that accurately fits in the inside diameter of the outer tube and is coaxially located inside the outer tube. For creating a flushing lumen between the inner tube and the outer tube, the inner tube is provided with an inward deformation running in longitudinal direction of the tube, seen in cross-sectional view of the tube, not exceeding 120°. The consequence of this local inward deformation is that the wall of the inner tube, seen in cross-sectional view of the tube, has an inwardly directed convex portion that connects to the remaining portion of the wall of the inner tube via rounded concave portions. In this way the lumen of the inner tube is reduced while at the same time a lumen is developed at the position of the inward deformation between the inner tube and the outer tube. The latter lumen is used as a flushing lumen for supplying the flushing fluid. The lumen, which is bounded by the inside wall of the inner tube is used as the ovum pick-up lumen. For a more detailed description and drawings of an arrangement according to this known state of the art, reference be made to Australian patent document AU-B-68184/87 mentioned above, whose contents, insofar as of importance for the present application, is deemed to be included herein by reference.

A similar arrangement is known from DE-A-3522782. In this arrangement however, the function of the two lumens is reversed.

The above-described known construction of an arrangement for transferring an ovum from a follicle has several disadvantages. The inner tube is to fit accurately within the outer tube, which necessitates accurate tolerances, both as regards the inside diameter of the outer tube and the outside diameter of the inner tube. Adhering to accurate tolerances always has a disadvantageous effect on the cost price. Another disadvantage is that the ovum pick-up lumen does not have a round cross section since the wall of the inner tube has a local inward deformation. Finally, when the point of the needle is made, for example by means of grinding, material is to be removed both from the outer tube and from the inner tube. In addition, the grinding is to be carried out with the flushing lumen in a certain orientation in order to guarantee that with the finished product the flushing lumen is in the right position relative to the point of the double lumen needle.

BRIEF SUMMARY OF THE INVENTION

It is an object of the invention to improve an arrangement of the type defined in the opening paragraph so that the above disadvantages are avoided and, in addition, advantages are provided which will be discussed hereinafter. For this purpose, the invention is characterized by the features stated in the characterizing part of claim 1.

The arrangement according to the invention has a number of characteristic advantages. The inner tube does not accurately fit in the outer tube, so that no accurate tolerances are necessary either for the outer tube or for the inner tube. The inner tube is made of a flexible material, so that the dimensions of the ovum pick-up lumen when an ovum passes can at least slightly adapt to the dimensions of the ovum. The flushing lumen is bounded by the inside wall of the inner tube, while the ovum lumen is bounded by the space between the outside wall of the inner tube and the inner wall of the outside tube. This implies that the flushing fluid used is in contact with metal only along the path from the distal end of the needle body to the outlet at the end remote from the distal needle end. This is deemed favourable. Metals are soluble in water only to a very small extent, it is true, but, nevertheless, an ovum should as much as possible be avoided contacting metals or fluids that have been in contact with metals. According to the state of the art, plastics can be manufactured having a composition that may be deemed utterly man-friendly.

The advantages of the invention turn out to be not only of a manufacturing nature, but also of importance for as good a protection of the ovum against possible damaging mechanical and chemical ambient influences during the transfer from the follicle to a receptacle, such as a glass test tube or the like to be connected to the outlet. Therefore, preferably an embodiment of the invention is utilized that is characterized in claim 2.

Claim 3 relates to a practical embodiment of the invention. In this embodiment the inner tube has such outside shape that the latter can be contiguous to the inside wall of the outer tube and thus over this part of the circumference has an outside diameter that is at least substantially equal to the inside diameter of the outer wall. The remaining, second part of the outside wall of the inner tube can elastically be deformed in the direction of the first portion. It will then be favourable when, during the passage of an ovum, the second part of the inner tube is deformed as far as possible in the direction of the first part. Alternatively, the flushing lumen should not be closed off completely when in that case too it is deemed desirable to have supply of flushing fluid.

Claim 4 relates to an embodiment of the arrangement according to the invention in which the inner tube is connected at least at the distal end by gluing it to the inside wall of the outer tube. In the description of this embodiment with reference to the drawings it will further appear that this embodiment can be designed so that during the grinding process of the point to the needle body at the distal end of the needle the inner tube need not be taken into account at all and the material of the inner tube need not be ground either.

For connecting the inner tube to the flushing inlet for supplying the flushing medium, the embodiment according to claim 5 is of importance. This embodiment is possible due to the flexibility of the inner tube as a result of which it is possible to feed-in the inner tube in a bend through an opening in the outer tube.

The invention will now be further explained with reference to the drawing which shows an embodiment of the invention exclusively by way of non-limiting example and wherein:

DETAILED DESCRIPTION OF THE INVENTION

Figure 1:
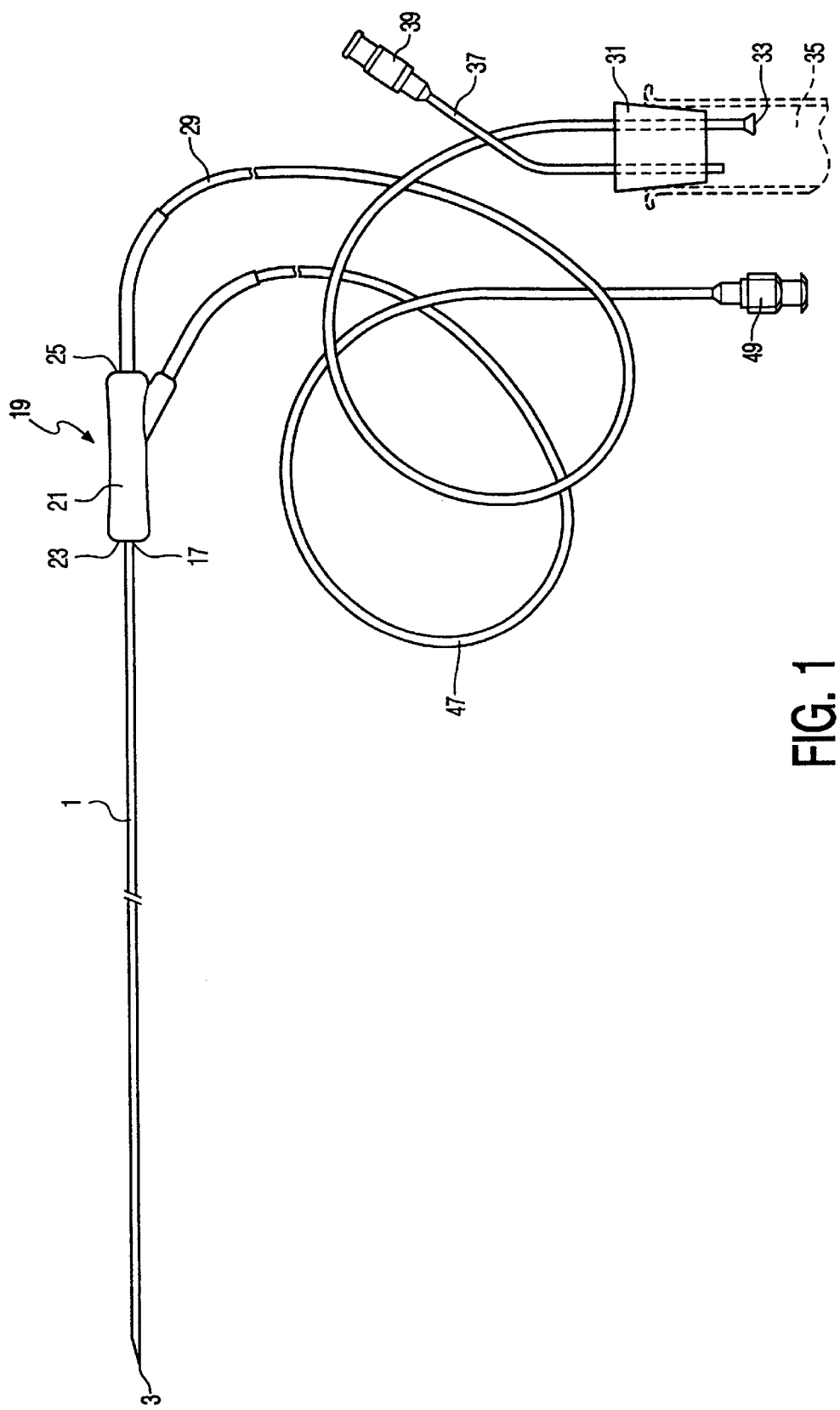
FIG. 1 shows a general side view of an arrangement according to the invention with a double lumen needle, a connector and tubings connected to the connector for supplying flushing fluid and discharging the ovum to the exterior.

Like elements in the various Figures are denoted by like reference characters.

Figure 2:
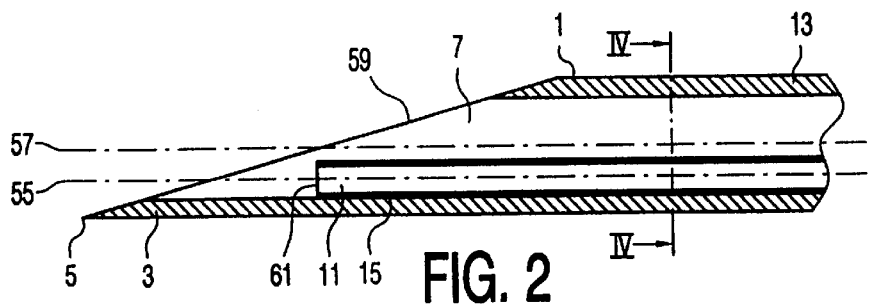
FIG. 2 shows a side view in cross section on an enlarged scale of a part of the needle body of the arrangement of FIG. 1 near the distal needle end.
Figure 3:
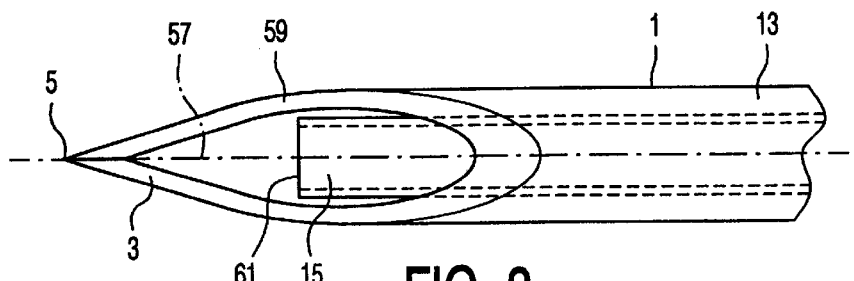
FIG. 3 shows a plan view of the needle end which is shown in FIG. 2.
Figure 4:
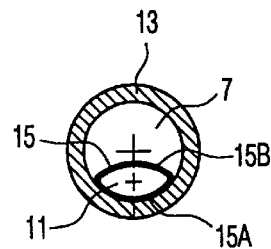
FIG. 4 shows a cross sectional view along the line IV—IV in FIG. 2.

The arrangement of FIG. 1 comprises a double lumen needle having an elongate needle body 1. As can be clearly seen in FIGS. 2, 3 and 5, there is a sharp point 5 at the distal needle end 3 to be inserted into the follicle, because the distal end is locally tapered. Near the end 3 of the needle there is an ovum pick-up lumen 7 present inside the needle body 1 for removing an ovum 9 from a follicle, see FIG. 5, as well as a flushing lumen 11 for inserting a flushing fluid into the follicle. The needle body comprises an outer tube with an inner tube 15 therein, which extends over at least part of the length of the outer tube 13.

Figure 7:
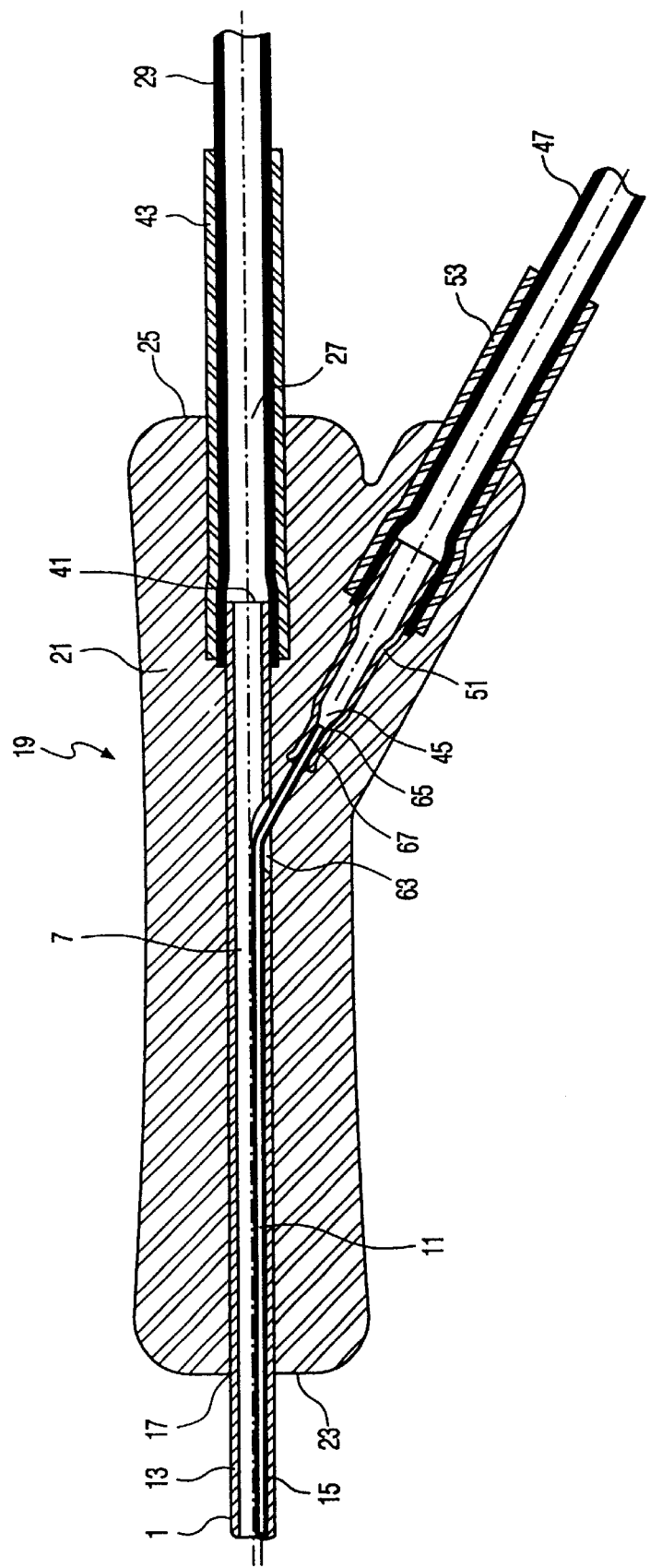
FIG. 7 shows a side view in cross section on an enlarged scale of the connector of the arrangement of FIG. 1 and of the parts of the arrangement which are connected to the connector.

The needle body 1 is connected to a connector 19 near the end 17 remote from the distal end 3, see FIGS. 1 and 7. The connector 19 has a connector body 21 which is connected at a first end 23 to the needle end 17 of the needle body 1, which end 17 is remote from the distal needle end. At a second end 25 the connector 19 has an inlet 27 for discharging the ovum 9 to the exterior. For this purpose, the connector 19 is connected to an ovum discharge tubing 29 of a suitable plastic material. At the end remote from the connector 19, the ovum discharge tubing 29 is included in a stopper 31 of a suitable elastic material, such as silicon rubber, the ovum discharge tubing 29 being passed through as far as a slightly flange-like end 33. The stopper 31 can be sealed in the neck of a glass receptacle 35. For creating a partial vacuum in the receptacle 35, a tube 37 is extended through the stopper 31 to the exterior, the end of which tube has a coupling 39 for a connection to a vacuum source. The outlet 27, see again FIG. 7, is connected to the ovum pick-up lumen 7 via a conduit means which are formed by a part of the ovum discharge tubing 29 and a part of the outer tube 13 of the needle body 1. As can be seen in FIG. 7, the ovum discharge tubing 29 at the free end 41 is slid fluid tight over the outside wall of the outer tube 13 of the needle body 1. To strengthen the connection from the ovum discharge tubing 29 to the connector 19, a strengthening sleeve 43 of an elastic plastic material which is slightly less flexible than the material of the ovum discharge tubing 29 is installed around the ovum discharge tubing near the second end 25 of the connector. The channel means between the outlet 27 and the needle body end 17 located opposite the distal end, which channel determines a first fluid pathway for the aspiration of an ovum 9 is thus formed by the parts of the outer tube 13 of the needle body that run inside the connector body 21 and the ovum discharge tubing 29 connected to it in a clamping and fluid tight fashion. By realising a partial vacuum in the receptacle 35 via the tube 37, at the end 3 of the needle body an ovum 9 can thus be aspirated from a follicle and transferred to the receptacle 35 via the ovum lumen 7 through the fluid pathway present in the connector 19 and through the ovum discharge tubing 29.

Between the two ends 23 and 25 of the connector body 21 there is a flushing inlet 45 for supplying a flushing medium. For this purpose, a flushing medium supply tubing 47 is present whose end has a coupling 49 for connection to a source of flushing medium. Inside the connector body 21 there is a connector tube 51 to which the tubing 47 is connected in a clamping and fluid tight fashion. Furthermore, a sleeve 53 resembling the sleeve 43 is present to strengthen the connection from the supply tubing 47 to the connector body 21. The flushing inlet 45 is in fluid communication to the flushing lumen 11 in a manner to be discussed in more detail for determining a second fluid pathway for flushing a follicle.

As will be apparent from the FIGS. 2 to 7, both fluid pathways inside the connector 19 and also inside the needle body 1 are completely separated.

The inner tube 15 in cross section has dimensions that are considerably smaller than the inside diameter of the outer tube 13, the inner tube 15 being made of a flexible plastic material selected for minimum presence of materials that might be harmful to the ovum 9. As is especially distinct in FIG. 4, the flushing medium 11 is bounded by the inside wall of the inner tube 15. The ovum lumen 7 is bounded by the space between the outside wall of the inner tube 15 and the inside wall of the outer tube 13.

Figure 5:
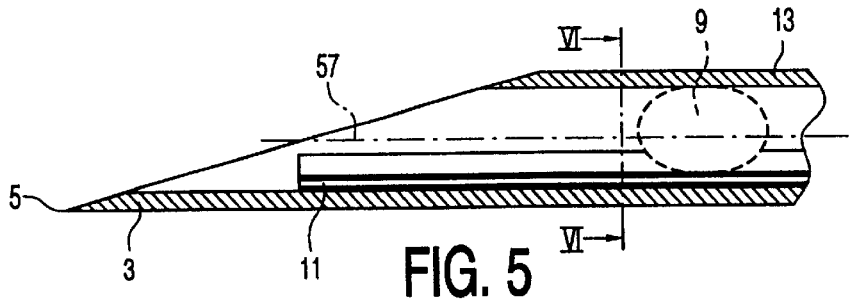
FIG. 5 shows once again a cross sectional view of FIG. 2, but now with a schematically shown ovum inside the ovum pick-up lumen.
Figure 6:
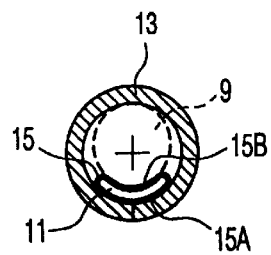
FIG. 6 shows a cross-sectional view of the double lumen needle according to the arrows VI—VI in FIG. 5.

The central axis 55 of the inner tube 15 is located eccentrically relative to the central axis 57 of the outer tube 13. This is especially distinct in FIG. 2. The outside wall of the inner tube 15 is located along a first part 15A of its circumference against the inside wall of the outer tube 13. The remaining second part 15B of the outside wall of the inner tube 15 is deformable under the influence of an external or internal pressure respectively, caused by the pressure exerted by an ovum 9 that passes while being aspirated by the ovum lumen 7 and the pressure of the flushing medium respectively, between a first position which is shown in FIGS. 5 and 6, in which the second part 15B lies closer to the first part 15A and a second position in which the second part 15B lies more remote from the first part 15A; see FIGS. 5 and 6. In essence, in said second position the inner tube 15 in the embodiment shown in cross section has more or less the shape of a double convex lens.

At the distal needle end 3 only the outer tube 13 of the needle body 1 is provided with a taper 59 tapering to a sharp point 5. Therefore, only the outer tube needs to be ground. The inner tube 15 is cut off straight at the distal end 61, at least in the embodiment shown. At that point and, if so required, also over a further part of the length, the inner tube is bonded to the inside wall of the outer tube 13 by means of gluing.

At a location within the connector 19, see again FIG. 7, the outer tube 13 has an opening 63 through the wall. Through this opening 63 the flexible inner tube 15 within the connector body 21 is led out. The inner tube 15 ends at the end 65 remote from the distal end 61 at a location outside the outer tube 13 and within the connector body 21, and within the tube 51 mentioned before. For this purpose, the tube has an end 67 with a cross section that is adapted to the cross section of the flexible tube 15. With suitable means such as glue, the inner tube 15 is attached in fluid tight fashion to the end 67 of the tube 51. In this way there is a fluid pathway from the coupling 49 through the supply tubing 47, the tube 51 and the inner tube 15 for supplying the flushing medium 11 for flushing a follicle. Since there is provided by means of suitable measures that between the circumference of the opening 63 and the enveloping part of the inner tube 15 there is a fluid-tight sealing material, for example of the connector body 21 or other material specifically provided for this purpose and not shown in the drawing, there is provided that a seal against fluid is locally present. The two fluid pathways mentioned earlier for the supply of a flushing medium and the discharge of an ovum are thus completely separated from each other and at the connector 19 no fluid leaks to the environment.

Albeit the invention has been explained with reference to only a sole example of embodiment, the invention is by no means restricted to this. On the contrary, the invention comprises any possible embodiment of an arrangement within the definition of claim 1. Those skilled in the art will appreciate that modifications and variations are possible. For example, the materials that are applied may be selected in accordance with the developing medical opinions and the developing technique in the field of materials. The inner tube 15 may have a different shape and be installed internally within the outer tube 13 in a different manner. The distal end of the inner tube may have a different shape than that shown in FIG. 3.

What is claimed is:

1. An arrangement for transferring an ovum from a follicle with a combined technique of simultaneous flushing and aspiration, the arrangement comprising:

a double lumen needle, comprising an elongate needle body having at the distal needle end to be inserted into the follicle an ovum pick-up lumen for removing an ovum from a follicle and a flushing lumen for inserting a flushing fluid into the follicle, the needle body comprising an outer tube with an internally located inner tube that extends over at least part of the length of the outer tube, the one lumen being bounded by the inside wall of the inner tube and the other lumen by the space between the outside wall of the inner tube and the inside wall of the outer tube, and a connector having a connector body which at a first end is connected to the needle and remote from the distal needle and, having an outlet at a second end for discharging the ovum to the exterior, having a channel means that connects the outlet at a second end for discharging the ovum to the exterior, having a channel means that connects the outlet to the ovum pick-up lumen and defines a first fluid pathway for aspirating an ovum and having a flushing inlet in between the two ends of the connector body for supplying the flushing medium and in fluid communication with the flushing lumen for defining a second fluid pathway for flushing a follicle, while the two fluid pathways within the connector and the needle body are separated from each other, wherein the inner tube in cross section has dimensions that are smaller than the inside diameter of the outer tube, wherein the inner tube is made of a flexible material, wherein the flushing lumen is bounded by the inside wall of the inner tube, and wherein the ovum lumen is bounded by the space between the outside wall of the inner tube and the inside wall of the outer tube.

2. An arrangement as claimed in claim 1, wherein the plastic of the inner tube is selected for minimum presence of materials that might be harmful to an ovum.

3. An arrangement as claimed in claim 1, wherein the central axis of the inner tube is located eccentrically relative to the central axis of the outer tube, wherein the outside wall of the inner tube along a first part of its circumference is contiguous to the inside wall of the outer tube, and wherein the remaining second part of the outside wall of the inner tube under the influence of a respective external and internal pressure, caused by an ovum passing by while being aspirated by the ovum lumen and the pressure of the flushing medium is elastically deformable between a respective first position in which the second part lies closer to the first part and a second position in which the second part lies more remote from the first part.

4. An arrangement as claimed in claim 3, wherein only the outer tube at the distal needle end of the needle body is provided with a taper tapering to a sharp cuspidated end, and wherein the inner tube at least at its distal end is connected by gluing to the inside wall of the outer tube.

5. An arrangement as claimed claim 1, wherein the outer tube located inboard of the connector has an opening passing through the wall, wherein the flexible inner tube inboard of the connector is lead out through the said opening in the outer tube, and wherein between the circumference of the said opening and the part of the inner tube passing through it, a fluid tight material is present.

* * * * *